United States Patent [19]

Krapcho et al.

[11] 3,931,169

[45] Jan. 6, 1976

[54] 5-SUBSTITUTED-PYRAZOLO(4,3-C)PYRIDINES

[75] Inventors: John Krapcho, Somerset; Chester Frank Turk, Kendall Park, both of N.J.

[73] Assignee: E. R. Squibb & Sons, Inc., Princeton, N.J.

[22] Filed: Jan. 29, 1975

[21] Appl. No.: 544,980

[52] U.S. Cl. .......... 260/240 R; 424/267; 260/293.55
[51] Int. Cl.² .......................................... C07D 471/02
[58] Field of Search .................. 260/293.55, 240 R

[56] References Cited
UNITED STATES PATENTS

| | | | |
|---|---|---|---|
| 3,423,414 | 1/1969 | Blatter | 260/293.55 X |
| 3,787,430 | 1/1974 | Hochn et al. | 260/240 R X |

*Primary Examiner*—Allen B. Curtis
*Attorney, Agent, or Firm*—Lawrence S. Levinson; Merle J. Smith; Burton Rodney

[57] ABSTRACT

Compounds of the formula

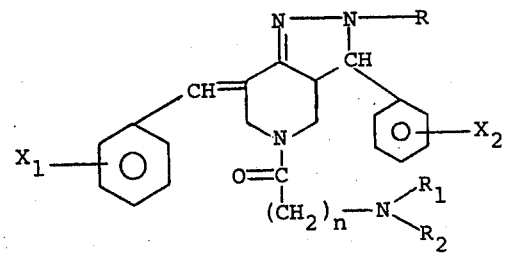

their N-oxides and acid addition salts thereof are provided which have been found to possess anti-inflammatory activity. In addition, methods for preparing such compounds, pharmaceutical compositions containing such compounds, and methods for using such compositions as anti-inflammatory agents are also provided.

16 Claims, No Drawings

5-SUBSTITUTED-PYRAZOLO(4,3-C)PYRIDINES

SUMMARY OF THE INVENTION

The present invention is directed to compounds of the formula

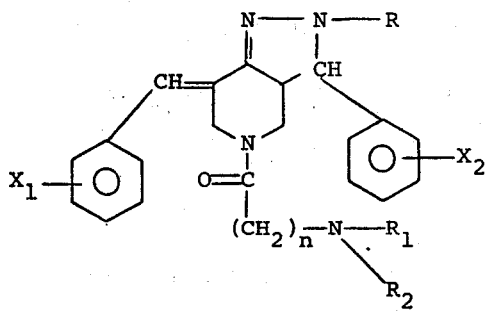

and N-oxides and acid addition salts thereof, wherein $X_1$ and $X_2$ can be the same or different and are hydrogen, F, Cl, lower alkyl, lower alkoxy, or $CF_3$; R is H, lower alkyl, phenyl lower alkyl, $X_1$ or $_2$-substituted phenyl lower alkyl, hydroxy lower alkyl or lower alkanoyl; $R_1$ and $R_2$ can be the same or different and are hydrogen or lower alkyl, and $R_1$, N and $R_2$ can be taken together to form a 5- or 6-membered heterocyclic ring which may include one other hetero atom such as sulfur, nitrogen or oxygen; and $n$ is 0 to 4. The foregoing compounds possess anti-inflammatory activity.

Preferred are those compounds of formula I wherein $X_1$ and $X_2$ are the same, $n$ is 0 or 1 and $R_1$ and $R_2$ are the same or different and are hydrogen or lowr alkyl. More preferred are those compounds wherein $X_1$ is hydrogen, $X_2$ is hydrogen, F, Cl, lower alkyl, lower alkoxy, or $CF_3$, $n$ is 0 or 1, and $R_1$ and $R_2$ are each hydrogen, or hydrogen and lower alkyl, respectively, or each the same or different lower alkyl. Most preferred are those compounds of formula I wherein $X_1$ and $X_2$ are hydrogen, $n$ is 0, and

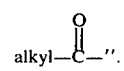

is $NH_2$ or $NHCH_3$, or $n$ is 1 and

is $N(CH_3)_2$.

In addition, this invention encompasses the methods for preparing said compounds, pharmaceutical compositions containing said compounds and methods for using said compositions as anti-inflammatory agents.

The term "lower alkyl" is intended to mean a straight or branched hydrocarbon fragment of from one to six carbon atoms.

The term "lower alkoxy" is intended to mean "lower alkyl-O—."

The term "lower alkanoyl" is intended to mean "lower $$\text{alkyl}-\overset{\overset{\displaystyle O}{\|}}{C}-".$$

The term "acid-addition salts" is intended to mean salts which may be formed for the purpose of isolation, purification and storage, such as the oxalate salt, etc. and pharmaceutically acceptable salts meant for administration of the compound to a host, such as the hydrochloride, sulfate, acetate, citrate, etc.

As indicated,

can be taken together to form a 5- or 6-membered heterocyclic ring, which heterocyclic ring includes piperidino, pyrrolidino, morpholino, thiamorpholino, piperazino and N-lower alkyl substituted piperazino.

The compounds of the present invention are prepared by reacting 4-piperidone II, or preferably an N-acyl derivative thereof, e.g., the N-acetyl or N-benzoyl derivative, with an aldehyde of the formula IIa, wherein $X_1$ is as previously defined, utilizing the procedure described in the Journal of the American Chemical Society, 70, 1824 (1948), which is incorporated by reference, to yield compounds of formula III.

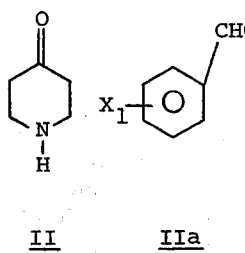 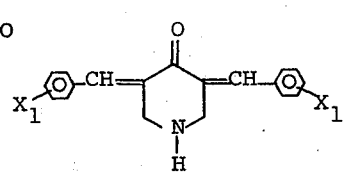 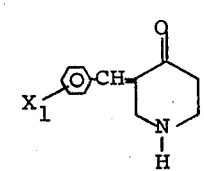

By adjusting the ratio of reactants so as to have an excess of the compound of formula II present, a compound of formula IV is obtained. A compound of formula III wherein each benzylidene substituent is different is prepared by reacting a compound of formula IV with an aldehyde of the structure IIb, wherein $X_2$ is different from $X_1$ of formula IIa.

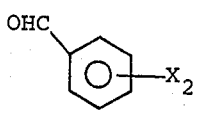

IIb

V

The compounds of formula III are generally isolated in the form of their acid-addition salts.

A compound of formula III, preferably an acid-addition salt such as the hydrochloride salt, sulfate salt, phosphate salt and so forth, is converted to a compound of formula V (wherein $X_1$ and $X_2$ are the same or different) by reaction with a hydrazine of the formula $H_2NNHR$, wherein R is hydrogen, lower alkyl, hydroxy lower alkyl wherein the alkyl group has from 1 to 8 carbon atoms, phenyl lower alkyl, or $X_1$-substituted phenyl lower alkyl wherein $X_1$ is as defined above. This reaction takes place in a polar organic solvent, preferably a water miscible alcohol at a temperature of from about 40°C to about 120°C, preferably at about the reflux temperature of the solvent, for from about ½ hour to about 12 hours, preferably from about 2 to about 6 hours. The resulting compounds of formula V are generally purified in the form of a mono- or di- acid addition salt.

The hydrazine of formula $H_2NNHR$ may be prepared according to known techniques, for example, by reacting chloramine, $NH_2Cl$, with an amine of the formula $RNH_2$.

Compounds of formula I wherein $n$ is an integer of from 0 to 4 may generally be prepared by reacting a compound of formula V (wherein $x_1$ and $X_2$ are the same or different) with a compound of the structure VI  $Cl-\overset{O}{\underset{\|}{C}}-(CH_2)_n Cl$ in the presence of an organic solvent, such as benzene, toluene, xylene, ethyl ether, dioxane or chloroform, and usually in the presence of an equivalent quantity of a base such as an amine, for example, triethylamine, or pyridine (in order to neutralize the HCl generated in the reaction), to form a compound of the structure

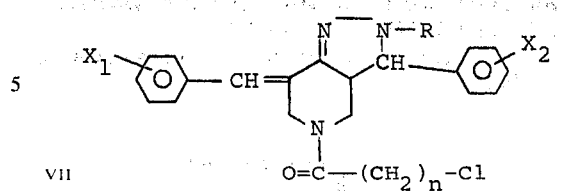

VII and reacting the formula VII compound with an amine of the structure

VIII  $HN\diagdown_{R_2}^{R_1}$

Compounds of formula I wherein $n$ is 0 and

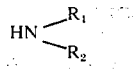

is $-NH(R_{1\ or\ 2})$ can also be prepared by reacting a compound of formula V (wherein $X_1$ and $X_2$ are the same or different) with an isocyanate of the structure IX  $R_{1\ or\ 2}-NCO$ in the presence of an organic solvent, such as benzene, toluene, xylene, ethyl ether or chloroform.

Compounds of formula I wherein $n$ is 0 and

is $NH_2$ may also be prepared by reacting a compound of formula V (wherein $X_1$ and $X_2$ are the same or different and prepared as described above) with KCNO or NaCNO.

In another method for preparing compounds of formula I, where $n$ is 0, compounds of formula V (wherein $X_1$ and $X_2$ are the same or different) may be reacted with a compound of the structure X  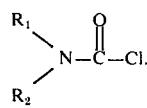

A compound of formula I wherein R is lower alkanoyl of from 1 to 7 carbon atoms is prepared by acylating a compound of formula I (wherein $X_1$ and $X_2$ are the same or different) wherein R is hydrogen employing conventional acylating agents under known conditions, for example, an acylating agent such as acetic anhydride or propionyl chloride and the like in an inert solvent, such as benzene, toluene, ether or tetrahydrofuran and so forth.

All of the starting materials in the above reactions as well as the reaction conditions and techniques are conventional in nature as will be apparent to one skilled in the art.

A compound of formula I may be converted to its N-oxide by reaction with an oxidizing agent such as hydrogen peroxide, peracetic acid and so forth.

The compounds of the present invention, their N-oxides, and their non-toxic pharmaceutically acceptable mono- or di-acid addition salts are useful as anti-inflammatory agents in mammalian species, e.g., rats and mice, when administered in amounts ranging from about 0.5 mg/kg to about 10.0 mg/kg of body weight per day. A preferred dosage regimen for optimum results is from about 1 mg to about 5 mg per kg of body weight per day, and such dosage units are employed that a total of about 35 mg to about 7 g of active ingredient are administered in a 24-hour period for a subject of about 70 kg body weight.

The compounds of the present invention in the described dosages may be administered orally; however, other routes such as intraperitoneally, subcutaneously, intramuscularly or intravenously may be employed.

The active compounds of the present invention are orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. The amount of active compound in such therapeutically useful compositions or preparations is such that a suitable dosage will be obtained.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit from is a capsule, it may contain in addition to materials of the above type a liquid carrier such as a fatty oil. Various other materials may be present as coatings or to otherwise modify the physical form of the dosage unit, for instance, tablets, pills or capsules may be coated with shellac, sugar, or both. A syrup of elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

The following examples illustrate the present invention, without, however, limiting the same thereto. All temperatures are expressed in degrees Centigrade.

EXAMPLE 1

2,3,3a,4,6,7-Hexahydro-N,2-dimethyl-3-phenyl-7-(phenylmethylene)-5H-pyrazolo[4,3-c]pyridine-5-carboxamide, hydrochloride A. 3,5-Bis(phenylmethylene)-4-piperidone, hydrochloride 14 g (0.1 mole) of N-acetyl-4-piperidone and 32 g (0.3 mole) of benzaldehyde in 150 ml of ethanol are cooled to 15° and treated dropwise with 33 ml of concentrated HCl, refluxed for 6 hours, and stored overnight at room temperature. The light yellow solid is filtered, washed with ethanol, then with ether and air-dried, weight 26 g (83%), mp. 273°–275°(dec.).

B.

3,3a,4,5,6,7-Hexahydro-2-methyl-3-phenyl-7-(phenylmethylene)-2H-pyrazolo-[4,3-c]pyridine, hydrochloride The product from A (9.5 g, 0.0305 mole) and 1.5 g (0.032 mole) of methylhydrazine in 200 ml of methanol is heated and the resulting solution refluxed for 4 hours. The solvent is removed on a rotary evaporator to yield a solid residue which on trituration with ether and cooling gives 9.5 g (92%) of the title compound, mp 210°–212°. Following crystallization from 250 ml of ethanol, the resulting light yellow material weighs 6.0 g (58%), mp 218°–220°.

C.

3,3a,4,5,6,7-Hexahydro-2-methyl-3-phenyl-7-(phenylmethylene)-2H-pyrazolo-[4,3-c]pyridine Fifteen g. (0.044 mole) of the product from B is suspended in 200 ml of $H_2O$ and 200 ml of 3:1-ether-$CHCl_3$, stirred, treated with 7 g of $K_2CO_3$, and the stirring continued until two clear layers are obtained. The layers are separated, the aqueous phase extracted with 3:1 ether-$CHCl_3$ (3 × 100 ml), the combined organic layers dried ($MgSO_4$), and the solvents evaporated. The mostly solid residue is triturated with hexane and cooled overnight, yield 11.7 g (87%) of colorless base; mp 115°–117°.

D.

2,3,3a,4,6,7-Hexahydro-N,2-dimethyl-3-phenyl-7-(phenylmethylene)-5H-pyrazolo-[4,3-c]pyridine-5-carboxamide, hydrochloride A stirred solution of the above base (C) (11.6 g, 0.038 mole) in 165 ml of benzene is treated dropwise with 2.7 g (0.047 mole) of methyl isocyanate, stirred at room temperature for 2 hours, refluxed for 4 hours, and kept overnight at room temperature. The benzene is evaporated to give 16.2 g of a crude urea compound as a brittle pale yellow residue.

The above is dissolved in 80 ml of $CH_3COC_2H_5$, cooled, and treated with 6.2 ml of 6.2 N alcoholic HCl. On rubbing, the crystalline HCl salt separates. After cooling overnight, the material is filtered, washed with cold $CH_3COC_2H_5$ and with ether, and dried in vacuo; wt., 14.3 g(94%); mp 169°–172° (foaming). Following crystallization from 100 ml MeOH-325 ml ether, the nearly colorless product weighs 12.2 g (80%); mp 170°–172°(foaming).

EXAMPLE 2

2,3,3a,4,6,7-Hexahydro-2-methyl-3-phenyl-7-(phenylmethylene)-5H-pyrazolo[4,3-c]pyridine-5-carboxamide A stirred solution of 10 g (0.033 mole) of the free base of Example 1C in 10 ml of acetic acid is diluted with 100 ml of $H_2O$ and treated with a solution of 3.0 g (0.034 mole) of 92% KCNO in 10 ml of $H_2O$; a yellow gummy product separates. After standing overnight at room temperature, 100 ml of $CHCl_3$ is added, the mixture stirred until two clear layers are obtained, the layers separated, the aqueous phase extracted with $CHCl_3$ (2 × 50 ml), the combined organic layers dried ($MgSO_4$), and the solvent evaporated to give 11.4 g of viscous yellow residue. The latter is triturated with 30 ml of boiling $CH_3CN$ and cooled overnight to give 6.1 g (54%) of yellow solid, mp 191°–193°.

EXAMPLE 3

5-[(Dimethylamino)acetyl]-3,3a,4,5,6,7-hexahydro-2-methyl-3-phenyl-7-(phenylmethylene)-2H-pyrazolo[4,3-c]pyridine

A.
5-Chloroacetyl-3,3a,4,5,6,7-hexahydro-2-methyl-3-phenyl-7-(phenylmethylene)-2H-pyrazolo[4,3-c]-pyridine A solution of 10 g (0.033 mole) of the base of Example 1C and 3.4 g (0.034 mole) of $(C_2H_5)_3N$ in 100 ml of benzene is added portionwise at 7°–10° to a stirred solution of 3 ml (0.038 mole) of $ClCOCH_2Cl$ in 100 ml of benzene. After the addition, the mixture is stirred at room temperature for 2 hours, refluxed for 1 hour, kept overnight at room temperature, stirred with 50 ml of $H_2O$, basified with 5 g of $K_2CO_3$, and the layers separated. The aqueous phase is extracted with ether (2 × 100 ml) and the combined organic layers dried ($MgSO_4$), and the solvents evaporated. The viscous residue (11.5 g) slowly becomes granular on triturating with 200 ml of boiling isopropyl ether and cooling overnight. The pale tan solid is filtered, washed with cold isopropyl ether, and air-dried; wt., 7.6 g (61 %); mp 88°–90° (s. 77°). IR: $6.0\mu$(strong).

B.
5-[(Dimethylamino)acetyl]-3,3a,4,5,6,7-hexahydro-2-methyl-3-phenyl-7-(phenylmethylene)-2H-pyrazolo[4,3-c]pyridine A slurry of 6.5 g (0.017 mole) of the product from A in 70 ml acetone is added to a stirred solution of 2.6 g (0.017 mole) sodium iodide in 70 ml of acetone and the resulting solution is refluxed for 3 hours. The cooled solution is filtered and the filtrate evaporated to give an oil residue. The oil residue is shaken with water and 500 ml of ethyl ether; the ether phase is separated, dried and the ether removed under reduced pressure. The residue is dissolved in 100 ml benzene and treated with a solution of 10 g (0.22 mole) of dimethylamine in 100 ml benzene. This solution is kept at room temperature for 5 days. The mixture is finally heated on a steam bath at 50°–75° for 4 hours, cooled, and treated with a solution of 4 g. of sodium hydroxide in 25 ml of water. The layers are separated and the organic phase washed with 25 ml of water and dried over anhydrous magnesium sulfate. Evaporation of the benzene leaves a viscous base which is crystallized from 20 ml of acetonitrile to give 3.6 g (55%) of solid; mp 132°–134°. Following recrystallization from 10 ml of acetonitrile, the light yellow product weighs 3.3 g (50%); mp 133°–135°.

EXAMPLE 4

5-[3-(Dimethylamino)propionyl]-3,3a,4,5,6,7-hexahydro-2-methyl-3-phenyl-7-(phenylmethylene)-2H-pyrazolo-[4,3-c]-pyridine, hydrochloride (1:2)

A. 5-(3-Chloropropionyl)-3,3a,4,5,6,7-hexahydro-2-methyl-3-phenyl-7-(phenylmethylene)-2H-pyrazolo[4,3-c]pyridine Ten g (0.033 mole) of the base of Example 1C is reacted with 3.7 ml (0.039 mole) of 3-chloropropionyl chloride in 200 ml of benzene in the presence of 3.4 g (0.034 mole) of triethylamine as described in Example 3A to give 14 g of crude, glass-like product. The latter is extracted with 350 ml of boiling diisopropyl ether (leaving a yellow-orange gummy material undissolved) and filtered. On rubbing and cooling, the pale yellow crystalline product separates, weighs 6.7 g (52%); mp 134°–136° (s. 130°).

B.
5-[3-(Dimethylamino)propionyl]-3,3a,4,5,6,7-hexahydro-2-methyl-3-phenyl-7-(phenylmethylene)-2H-pyrazolo[4,3-c]pyridine, hydrochloride (1:2)

The above material (A) (6.7 g; 0.017 mole) is reacted first with 2.6 g (0.017 mole) of NaI in 70 ml of acetone, then with 10 g (0.22 mole) of dimethylamine in 100 ml of benzene as described in Example 3B to give 7.5 g of crude syrupy base. The latter (6.5 g) is dissolved in 65 ml of methylethylketone, stirred, and treated with 3.9 ml of 8.2 N alcoholic HCl to precipitate the 2HCl salt as a gum which crystallizes on rubbing and cooling to give 7.1 g (100%) product, mp 110°–122°(foaming); s. 80°. Following crystallization from 30 ml methanol-60 ml ethyl ether, the cream-colored solid weighs 5.5 g (78%); mp 162°–164° (s. 158°).

EXAMPLES 5 to 15

Following the procedure of Example 1 but substituting for benzaldehyde in part A, the compound indicated in column I, there is obtained the corresponding compound of formula I (corresponding to Example 1) wherein each X (that is $X_1$ and $X_2$), and its position, is as indicated in column II:

| Example | I | II |
|---|---|---|
| 5. | o-chlorobenzaldehyde | 2-chloro |
| 6. | p-chlorobenzaldehyde | 4-chloro |
| 7. | p-fluorobenzaldehyde | 4-fluoro |
| 8. | 2-methylbenzaldehyde | 2-methyl |
| 9. | 3-methylbenzaldehyde | 3-methyl |
| 10. | 4-methylbenzaldehyde | 4-methyl |
| 11. | 2-methoxybenzaldehyde | 2-methoxy |
| 12. | 3-methoxybenzaldehyde | 3-methoxy |
| 13. | 4-methoxybenzaldehyde | 4-methoxy |
| 14. | 4-butoxybenzaldehyde | 4-butoxy |
| 15. | 3-trifluoromethylbenzaldehyde | 3-trifluoromethyl |

EXAMPLES 16 to 26

Following the procedure of Example 1 and Example 2 but substituting for benzaldehyde in Example 1 part A, the compound indicated in column I, there is obtained the corresponding compound of formula I (corresponding to the compound formed in Example 2) wherein each X (that is $X_1$ and $X_2$), and its position, is as indicated in column II:

| Example | I | II |
|---|---|---|
| 16. | o-chlorobenzaldehyde | 2-chloro |
| 17. | p-chlorobenzaldehyde | 4-chloro |
| 18. | p-fluorobenzaldehyde | 4-fluoro |
| 19. | 2-ethylbenzaldehyde | 2-ethyl |
| 20. | 3-methylbenzaldehyde | 3-methyl |
| 21. | 4-propylbenzaldehyde | 4-propyl |
| 22. | 2-methoxybenzaldehyde | 2-methoxy |
| 23. | 3-ethoxybenzaldehyde | 3-ethoxy |
| 24. | 4-propoxybenzaldehyde | 4-propoxy |
| 25. | 3-butoxybenzaldehyde | 3-butoxy |
| 26. | 4-trifluoromethylbenzaldehyde | 4-trifluoromethyl |

EXAMPLES 27 to 37

Following the procedure of Example 1 and Example 3 but substituting for benzaldehyde in Example 1 part A, the compound indicated in column I, there is obtained the corresponding compound of formula I (corresponding to the compound formed in Example 3) wherein each X (that is $X_1$ and $X_2$), and its position, is as indicated in column II:

| Example | I | II |
|---|---|---|
| 27. | o-chlorobenzaldehyde | 2-chloro |
| 28. | p-chlorobenzaldehyde | 4-chloro |
| 29. | p-fluorobenzaldehyde | 4-fluoro |
| 30. | 2-methylbenzaldehyde | 2-methyl |
| 31. | 3-methylbenzaldehyde | 3-methyl |
| 32. | 4-methylbenzaldehyde | 4-methyl |
| 33. | 2-methoxybenzaldehyde | 2-methoxy |
| 34. | 3-methoxybenzaldehyde | 3-methoxy |
| 35. | 4-methoxybenzaldehyde | 4-methoxy |
| 36. | 4-butoxybenzaldehyde | 4-butoxy |
| 37. | 3-trifluoromethylbenzaldehyde | 3-trifluoromethyl |

EXAMPLES 38 – 55

Following the procedure of Example 1 but substituting for methylhydrazine in part B, the compound indicated in column I, there is obtained the corresponding compound of formula I (corresponding to Example 1) wherein R is the group indicated in column II:

| Example | I | II |
|---|---|---|
| 38. | ethylhydrazine | ethyl |
| 39. | propylhydrazine | propyl |
| 40. | isopropylhydrazine | isopropyl |
| 41. | isobutylhydrazine | isobutyl |
| 42. | butylhydrazine | butyl |
| 43. | (2-hydroxyethyl)hydrazine | 2-hydroxyethyl |
| 44. | 3-hydroxypropyl hydrazine | 3-hydroxypropyl |
| 45. | benzylhydrazine | benzyl |
| 46. | phenethylhydrazine | phenethyl |
| 47. | o-fluorobenzylhydrazine | o-fluorobenzyl |
| 48. | m-chlorophenethylhydrazine | m-chlorophenethyl |
| 49. | p-trifluoromethylbenzyl-hydrazine | p-trifluoromethyl-benzyl |
| 50. | m-methylbenzylhydrazine | m-methylbenzyl |
| 51. | o-ethylphenethylhydrazine | o-ethylphenethyl |
| 52. | m-methoxybenzylhydrazine | m-methoxybenzyl |
| 53. | p-ethoxyphenethylhydrazine | p-ethoxyphenethyl |
| 54. | 3-phenylpropyl hydrazine | 3-phenylpropyl |
| 55. | hydrazine | hydrogen |

EXAMPLES 56 – 73

Following the procedure of Example 1 and Example 2 but substituting for methylhydrazine in Example 1 part B, the compound indicated in column I, there is obtained the corresponding compound of formula I (corresponding to Example 2) wherein R is the group indicated in column II:

| Example | I | II |
|---|---|---|
| 56. | ethylhydrazine | ethyl |
| 57. | propylhydrazine | propyl |
| 58. | isopropylhydrazine | isopropyl |
| 59. | isobutylhydrazine | isobutyl |
| 60. | hexylhydrazine | hexyl |
| 61. | (4-hydroxybutyl)hydrazine | 4-hydroxybutyl |
| 62. | 3-hydroxypropyl hydrazine | 3-hydroxypropyl |
| 63. | benzylhydrazine | benzyl |
| 64. | phenethylhydrazine | phenethyl |
| 65. | o-fluorobenzylhydrazine | o-fluorobenzyl |
| 66. | m-chlorophenethylhydrazine | m-chlorophenethyl |
| 67. | p-trifluoromethylbenzyl-hydrazine | p-trifluoromethyl-benzyl |
| 68. | m-methylbenzylhydrazine | m-methylbenzyl |
| 69. | o-ethylphenethylhydrazine | o-ethylphenethyl |
| 70. | m-methoxybenzylhydrazine | m-methoxybenzyl |

-continued

| Example | I | II |
|---|---|---|
| 71. | p-ethoxyphenylethylhydrazine | p-ethoxyphenethyl |
| 72. | 3-phenylpropyl hydrazine | 3-phenylpropyl |
| 73. | hydrazine | hydrogen |

EXAMPLES 74 – 91

Following the procedure of Example 1 and Example 4 but substituting for methylhydrazine in Example 1 part B, the compound indicated in column I, there is obtained the corresponding compound of formula I (corresponding to Example 4) wherein R is the group indicated in column II:

| Example | I | II |
|---|---|---|
| 74. | ethylhydrazine | ethyl |
| 75. | propylhydrazine | propyl |
| 76. | isopropylhydrazine | isopropyl |
| 77. | isobutylhydrazine | isobutyl |
| 78. | butylhydrazine | butyl |
| 79. | (2-hydroxyethyl)hydrazine | 2-hydroxyethyl |
| 80. | 3-hydroxypropyl hydrazine | 3-hydroxypropyl |
| 81. | benzylhydrazine | benzyl |
| 82. | phenethylhydrazine | phenethyl |
| 83. | o-fluorobenzylhydrazine | o-fluorobenzyl |
| 84. | m-chlorophenethylhydrazine | m-chlorophenethyl |
| 85. | p-trifluoromethylbenzyl-hydrazine | p-trifluoromethyl-benzyl |
| 86. | m-methylbenzylhydrazine | m-methylbenzyl |
| 87. | o-ethylphenethylhydrazine | o-ethylphenethyl |
| 88. | m-methoxybenzylhydrazine | m-methoxybenzyl |
| 89. | p-ethoxyphenethylhydrazine | p-ethoxyphenethyl |
| 90. | 3-phenylpropyl hydrazine | 3-phenylpropyl |
| 91. | hydrazine | hydrogen |

EXAMPLES 92 – 96

Following the procedure of Example 1 but substituting for the methyl isocyanate in part D, the compound indicated in column I, there is obtained the corresponding compound of formula I (corresponding to Example 1) wherein the

group is as indicated in column II.

| Example | I | II |
|---|---|---|
| 92. | ethyl isocyanate | —NH($C_2H_5$) |
| 93. | butyl isocyanate | —NH($C_4H_9$) |
| 94. | hexyl isocyanate | —NH($C_6H_{13}$) |
| 95. | propyl isocyanate | —NH($C_3H_7$) |
| 96. | amyl isocyanate | —NH($C_5H_{11}$) |

EXAMPLES 97 – 107

Following the procedure of Example 3 but substituting for the dimethylamine, the compound shown in column I below, there is obtained the corresponding compound of formula I (corresponding to Example 3) wherein the

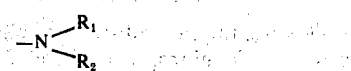

group is as indicated in column II:

| Example | I | II |
|---|---|---|
| 97. | piperidine | piperidino |
| 98. | morpholine | morpholino |
| 99. | thiamorpholine | thiamorpholino |
| 100. | pyrrolidine | pyrrolidino |
| 101. | piperazine | piperazino |
| 102. | N-methylpiperazine | N-methylpiperazino |
| 103. | N-ethylpiperazine | N-ethylpiperazino |
| 104. | N-propylpiperazine | N-propylpiperazino |
| 105. | N-butylpiperazine | N-butylpiperazino |
| 106. | N-amylpiperazine | N-amylpiperazino |
| 107. | N-hexylpiperazine | N-hexylpiperazino | obtained the corresponding compound of formula I (corresponding to Example 4) wherein n and

are indicated in column III:

| Example | I | II | $\underline{n}$ | $-N\!\!<\!\!^{R_1}_{R_2}$ |
|---|---|---|---|---|
| 108. | $Cl-\overset{O}{\underset{\|}{C}}-(CH_2)_3-Cl$ | $HN\!\!<\!\!^{C_2H_5}_{CH_3}$ | 3 | $-N\!\!<\!\!^{C_2H_5}_{CH_3}$ |
| 109. | $Cl-\overset{O}{\underset{\|}{C}}-(CH_2)_4-Cl$ | $HN\!\!<\!\!^{t-C_4H_9}_{CH_3}$ | 4 | $-N\!\!<\!\!^{t-C_4H_9}_{CH_3}$ |
| 110. | $Cl-\overset{O}{\underset{\|}{C}}-(CH_2)_2-Cl$ | $HN\!\!<\!\!^{C_3H_7}_{C_5H_{11}}$ | 2 | $-N\!\!<\!\!^{C_3H_7}_{C_5H_{11}}$ |
| 111. | $Cl-\overset{O}{\underset{\|}{C}}-CH_2-Cl$ | $HN\!\!<\!\!^{C_2H_5}_{C_2H_5}$ | 1 | $-N\!\!<\!\!^{C_2H_5}_{C_2H_5}$ |
| 112. | $Cl-\overset{O}{\underset{\|}{C}}-(CH_2)_3-Cl$ | HN⟩ (piperidine) | 3 | -N⟩ |
| 113. | $Cl-\overset{O}{\underset{\|}{C}}-(CH_2)_2-Cl$ | HN⟩NH (piperazine) | 2 | -N⟩NH |
| 114. | $Cl-\overset{O}{\underset{\|}{C}}-Cl$ | HN⟩N—C₂H₅ | 0 | -N⟩N—C₂H₅ |
| 115. | $Cl-\overset{O}{\underset{\|}{C}}-(CH_2)_3-Cl$ | HN⟩O (morpholine) | 3 | -N⟩O |
| 116. | $Cl-\overset{O}{\underset{\|}{C}}-(CH_2)_3-Cl$ | HN⟩ (pyrrolidine) | 3 | -N⟩ |
| 117. | $Cl-\overset{O}{\underset{\|}{C}}-(CH_2)_4-Cl$ | HN⟩S (thiamorpholine) | 4 | -N⟩S |
| 118. | $Cl-\overset{O}{\underset{\|}{C}}-Cl$ | $HNH(C_2H_5)$ | 0 | $-NH(C_2H_5)$ |
| 119. | $Cl-\overset{O}{\underset{\|}{C}}-(CH_2)_4-Cl$ | $HNH(C_4H_9)$ | 4 | $-NH(C_4H_9)$ |
| 120. | $Cl-\overset{O}{\underset{\|}{C}}-(CH_2)_2-Cl$ | $HNH(CH_3)$ | 2 | $-NH(CH_3)$ |

EXAMPLES 108 – 120

Following the procedure of Example 4 but substituting for the 3-chloropropionyl chloride the compound indicated in column I and substituting for the dimethylamine the compound indicated in column II, there is

EXAMPLES 121 – 133

Following the procedure of Example 1 and Example 4 but substituting for the benzaldehyde (in part A of Example 1), the compound indicated in column I, substituting for the methylhydrazine, the compound indicated in column II, substituting for the 3-chloropropionyl chloride, the compound indicated in column III, and substituting for the dimethylamine, the compound indicated in column IV, there is obtained the corresponding compound of formula I wherein $X_1$, $X_2$, R, $n$ and $$-N\begin{matrix}R_1\\R_2\end{matrix}$$

are as indicated in column V:

| Example | I<br>$X_1$<br>R | II<br>H₂NNHR | III<br>Cl–C(O)–(CH₂)ₙ–Cl | IV<br>HN(R₁)(R₂) | V<br>$X_1$<br>R | $X_2$ | R | n | $-N(R_1)(R_2)$ |
|---|---|---|---|---|---|---|---|---|---|
| 121. | o—F | H | Cl–C(O)–(CH₂)₃–Cl | HN(C₂H₅)(CH₃) | o—fluoro | same as X₁ | H | 3 | —N(C₂H₅)(CH₃) |
| 122. | p—Cl | C₂H₅ | Cl–C(O)–(CH₂)₄–Cl | HN(t—C₄H₉)(C₂H₅) | p—Cl | " | C₂H₅ | 4 | —N(t—C₄H₉)(C₂H₅) |
| 123. | 3—C₂H₅ | 2—C₂H₄OH | Cl–C(O)–(CH₂)₂–Cl | HN(C₃H₇)(C₅H₁₁) | 3—C₂H₅ | " | 2—C₂H₄OH | 2 | —N(C₃H₇)(C₅H₁₁) |
| 124. | 4—CH₃O | C₆H₅CH₂ | Cl–C(O)–CH₂–Cl | HN(C₂H₅)(C₂H₅) | 4—CH₃O | " | C₆H₅CH₂ | 1 | —N(C₂H₅)(C₂H₅) |
| 125. | 4—CF₃ | m—CH₃—C₆H₅CH₂ | Cl–C(O)–(CH₂)₃–Cl | HN⟨O⟩ (piperidine) | 4—CF₃ | " | m—CH₃—C₆H₅CH₂ | 3 | —N⟨O⟩ |
| 126. | 3—C₄H₉O | CH₃C(O)— | Cl–C(O)–(CH₂)₂–Cl | HN(piperazine)NH | 3—C₄H₉O | " | CH₃C(O) | 2 | —N(piperazine)NH |
| 127. | H | C₆H₅C₂H₄ | Cl–C(O)–(CH₂)₄–Cl | HN(N—C₂H₅) | H | " | C₆H₅C₂H₄ | 4 | —N(N—C₂H₅) |
| 128. | 3—C₃H₇O | o—F—C₆H₅—CH₂ | Cl–C(O)–(CH₂)₃–Cl | HN⟨O⟩ (morpholine) | 3—C₃H₇O | " | o—F—C₆H₅—CH₂ | 3 | —N⟨O⟩ |
| 129. | 2—C₂H₅ | H | Cl–C(O)–(CH₂)₃–Cl | HN (pyrrolidine) | 2—C₂H₅ | " | H | 3 | —N (pyrrolidine) |
| 130. | 3—C₂H₅O | C₃H₇ | Cl–C(O)–Cl | HN⟨S⟩ (thiomorpholine) | 3—C₂H₅O | " | C₃H₇ | 0 | —N⟨S⟩ |
| 131. | 4—C₅H₁₁ | H | Cl–C(O)–(CH₂)₃–Cl | HNH(C₂H₅) | 4—C₅H₁₁ | " | H | 3 | —NH(C₂H₅) |
| 132. | 4—C₆H₁₃O | C₂H₅C(O) | Cl–C(O)–(CH₂)₄–Cl | HNH(C₄H₉) | 4—C₆H₁₃O | " | C₂H₅C(O) | 4 | —NH(C₄H₉) |
| 133. | o—Cl | C₆H₅CH₂ | Cl–C(O)–(CH₂)₂–Cl | HNH(CH₃) | o—Cl | " | C₆H₅CH₂ | 2 | —NH(CH₃) |

EXAMPLE 134

2-Acetyl-2,3,3a,4,6,7-hexahydro-N-methyl-3-phenyl-7-(phenylmethylene)-5H-pyrazolo[4,3-c]pyridine-5-carboxamide A suspension of 5 g of 2,3,3a,4,6,7-hexahydro-N-methyl-3-phenyl-7-(phenylmethylene)-5H-pyrazolo[4,3-c]pyridine-5-carboxamide (the product of Example 55) in 50 ml of acetic anhydride is refluxed for four hours. The mixture is cooled and poured onto 250 ml of ice-water. The product is filtered and dried.

EXAMPLE 135

Interaction of equivalent quantities of an $X_1$-substituted benzaldehyde and N-acetyl-4-piperidone according to the procedure of Example 1 yields the 3-($X_1$-substitued benzylidene)-4-piperidone hydrochloride. The latter is purified by crystallization of the hydrochloride salt or by distillation of the free base and then reacted with an equivalent quantity of $X_2$-substituted benzaldehyde to give 3-($X_1$-substituted benzylidine)-5-($X_2$-substituted benzylidene)-4-piperidone hydrochloride. These intermediates are converted to compounds of Formula I utilizing the procedures used in Examples 1 to 4.

EXAMPLE 136

5-[(Dimethylamino)acetyl]-3,3a,4,5,6,7-hexahydro-2-methyl-3-phenyl-7-(phenylmethylene)-2H-pyrazolo[4,3-c]pyridine N-oxide A solution of the free base of the product of Example 3 in acetic acid is treated with an equivalent quantity of 30% hydrogen peroxide and the solution then heated at 80°–90° for 1 hour and cooled. The solvent is then removed on a rotary evaporator at reduced pressure to yield the title compound.

EXAMPLE 137

Preparation of capsule formulation

| Ingredient | Milligrams per Capsule |
| --- | --- |
| 2,3,3a,4,6,7-hexahydro-N,2-dimethyl-3-phenyl-7-(phenylmethylene)-5H-pyrazolo[4,3-c]pyridine-5-carboxamide hydrochloride | 400 |
| Starch | 80 |
| Magnesium stearate | 5 |

The active ingredient, starch and magnesium stearate are blended together. The mixture is used to fill hard shell capsules of a suitable size at a fill weight of 485 milligrams per capsule.

EXAMPLE 138

Preparation of tablet formulation

| Ingredient | Milligrams per Tablet |
| --- | --- |
| 2,3,3a,4,6,7-hexahydro-2-methyl-3-phenyl-7-(phenylmethylene)-5H-pyrazolo-[4,3-c]pyridine-5-carboxamide | 300 |
| Lactose | 200 |
| Corn starch (for mix) | 50 |
| Corn starch (for paste) | 50 |
| Magnesium stearate | 6 |

The active ingredient, lactose and corn starch (for mix) are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at 120°F. The dry granules are passed through a No. 16 screen. The mixture is lubricated with magnesium stearate and compressed into tablets in a suitable tableting machine. Each tablet contains 300 milligrams of active ingredient.

EXAMPLE 139

Preparation of oral syrup formulation

| Ingredient | Amount |
| --- | --- |
| 5-[3-(Dimethylamino)propionyl]-3,3a,4,5,6,7-hexahydro-2-methyl-3-phenyl-7-(phenylmethylene)-2H-pyrazolo-[4,3-c]pyridine, hydrochloride (1:2) | 500 mg. |
| Sorbitol solution (70% N.F.) | 40 ml. |
| Sodium benzoate | 150 mg. |
| Sucaryl | 90 mg. |
| Saccharin | 10 mg. |
| Red Dye (F.D. & C. No. 2) | 10 mg. |
| Cherry flavor | 50 mg. |
| Distilled water qs to | 100 ml. |

The sorbitol solution is added to 40 milliliters of distilled water and the active ingredient is suspended therein. The sucaryl, saccharin, sodium benzoate, flavor and dye are added and dissolved in the above solution. The volume is adjusted to 100 milliliters with distilled water.

Other ingredients may replace those listed in the above formulation. For example, a suspending agent such as bentonite magma, tragacanth, carboxymethylcellulose, or methylcellulose may be used. Phosphates, citrates or tartrates may be added as buffers. Preservatives may include the parabens, sorbic acid and the like and other flavors and dyes may be used in place of those listed above.

What is claimed is:

1. A compound of the formula

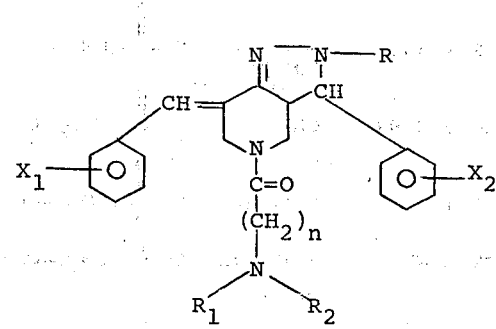

wherein $X_1$ and $X_2$ are the same or different and are selected from the group consisting of hydrogen, F, cl, lower alkyl, lower alkoxy, or $CF_3$; R is selected from the group consisting of hydrogen, lower alkyl, phenyl lower alkyl, $x_{1\ or\ 2}$- substituted phenyl lower alkyl wherein $X_{1\ or\ 2}$ is as previously defined, hydroxy lower alkyl or lower alkanoyl; $R_1$ and $R_2$ are the same or different and are selected from the group consisting of hydrogen or lower alkyl or

may be taken together to form a 5- or 6-membered heterocyclic ring which may include one other heteroatom selected from the group consisting of sulfur, nitrogen or oxygen; and $n$ is 0 to 4; and N-oxides and pharmaceutically acceptable acid addition salts thereof.

2. A compound as defined in claim 1 wherein $X_1$ and $X_2$ are the same.

3. A compound as defined in claim 1 wherein $X_1$ and $X_2$ are hydrogen.

4. A compound as defined in claim 1 wherein one of $X_1$ and $X_2$ is hydrogen.

5. A compound as defined in claim 1 wherein $X_1$ and $X_2$ are the same or different and are selected from the group consisting of hydrogen, lower alkyl, F or Cl.

6. A compound as defined in claim 1 wherein $X_1$ and $X_2$ are the same or different and are selected from the group consisting of hydrogen, lower alkoxy or $CF_3$.

7. A compound as defined in claim 1 wherein R is selected from the group consisting of hydrogen and lower alkyl.

8. A compound as defined in claim 7 wherein R is selected from the group consisting of hydrogen, lower alkyl, and hydroxy lower alkyl.

9. A compound as defined in claim 1 wherein R is phenyl lower alkyl or $X_{1\ or\ 2}$-substituted phenyl lower alkyl.

10. A compound as defined in claim 1 wherein $n$ is 0, 1 or 2.

11. A compound as defined in claim 10 wherein $X_1$ and $X_2$ are hydrogen, and R is methyl.

12. A compound of claim 1 having the name 2,3,3a,4,6,7-hexahydro-N-2-dimethyl-3-phenyl-7-(phenylmethylene)-5H-pyrazolo-[4,3-c]pyridine-5-carboxamide.

13. A compound as defined in claim 1 having the name 2,3,3a,4,6,7-hexahydro-2-methyl-3-phenyl-7-(phenylmethylene)-5H-pyrazolo[4,3-c]pyridine-5 carboxamide.

14. A compound as defined in claim 1 having the name 5-[(dimethylamino)acetyl]-3,3a,4,5,6,7-hexahydro-2-methyl-3-phenyl-7-(phenylmethylene)-2H-pyrazolo[4,3-c]pyridine.

15. A compound as defined in claim 1 having the name 5-[3-(Dimethylamino)propionyl]-3,3a,4,5,6,7-hexahydro-2-methyl-3-phenyl-7-(phenylmethylene)-2H-pyrazolo-[4,3-c]pyridine.

16. A compound of claim 1 wherein

is selected from the group consisting of piperidino, pyrrolidino, morpholino, thiamorpholino, piperazino and N-lower alkyl piperazino.

* * * * *

UNITED STATES PATENT AND TRADEMARK OFFICE
CERTIFICATE OF CORRECTION

PATENT NO. : 3,931,169
DATED : January 6, 1976
INVENTOR(S) : John Krapcho et al.

It is certified that error appears in the above-identified patent and that said Letters Patent are hereby corrected as shown below:

Column 1, line 35, "lowr" should read --lower--.
Column 3, line 49, "witfh" should read --with--.
Column 3, line 53, "x$_1$" should read --X$_1$--.
Column 5, line 41, "from" should read --form--.
Column 13, Example 126, Column II (R), the formula should read $--CH_3\overset{O}{\underset{\|}{C}}-$ --.

Column 14, Example 126, Column V (R), the formula should read $--CH_3\overset{O}{\underset{\|}{C}}-$ --.

Column 13, Example 132, Column II (R), the formula should read $--C_2H_5\overset{O}{\underset{\|}{C}}-$ --.

Column 16, line 60, "cl" should read --Cl--.

Signed and Sealed this eleventh Day of May 1976

[SEAL]

Attest:

RUTH C. MASON
Attesting Officer

C. MARSHALL DANN
Commissioner of Patents and Trademarks